(12) United States Patent
Ramachandran et al.

(10) Patent No.: US 9,988,402 B2
(45) Date of Patent: *Jun. 5, 2018

(54) AMINE-BORANES BEARING BORANE-INTOLERANT FUNCTIONALITIES

(71) Applicant: Purdue Research Foundation, West Lafayette, IN (US)

(72) Inventors: P Veeraraghavan Ramachandran, West Lafayette, IN (US); Ameya Sanjay Kulkarni, West Lafayette, IN (US)

(73) Assignee: PURDUE RESEARCH FOUNDATION, West Lafayette, IN (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/680,259

(22) Filed: Aug. 18, 2017

(65) Prior Publication Data

US 2018/0051040 A1 Feb. 22, 2018

Related U.S. Application Data

(60) Provisional application No. 62/377,290, filed on Aug. 19, 2016.

(51) Int. Cl.
*C07F 5/02* (2006.01)
*C07F 7/18* (2006.01)
*C01B 35/14* (2006.01)

(52) U.S. Cl.
CPC ............ *C07F 5/022* (2013.01); *C01B 35/146* (2013.01); *C07F 7/1848* (2013.01)

(58) Field of Classification Search
None
See application file for complete search history.

(56) References Cited

U.S. PATENT DOCUMENTS

| | | | | |
|---|---|---|---|---|
| 5,516,909 A | * | 5/1996 | Sullivan | ............... C07D 333/58 546/13 |
| 6,346,532 B1 | | 2/2002 | Maruyama | |
| 9,834,448 B2 | * | 12/2017 | Ramachandran | ..... C01B 35/146 |
| 2010/0130780 A1 | * | 5/2010 | Cartolano | ............... C07F 5/006 564/8 |
| 2016/0101984 A1 | * | 4/2016 | Ramachandran | ....... C07F 5/027 423/285 |

OTHER PUBLICATIONS

Brotherton ("Boron Compounds" Ullmann's Encyclopedia of Industrial Chemistry, 2000, p. 237-258) (Year: 2000).*
B. Carboni, et al., "Recent Developments in the Chemistry of Amine- and Phosphine-Boranes." Tetrahedron 55 (1999) 1197-1248.
P.V. Ramachandran, et al., "Amine-Boranes: Green Hypergolic Fuels with Consistently Low Ignition Delays." Chem. Eur. J. 2014, 20, 168969-16872.
K. Adamczyk, et al., "Real-Time Observation of Carbonic Acid Formation in Aqueous Solution." Science 326 (5960), 1690-1694 (2009).
E. Brehm, et al., "Investigation of the origin and synthetic application of the pseudodilution effect for Pd-catalyzed macrocyclisations in concentrated solutions with immobilized catalysts." Org. Biomol. Chem., 2013, 11, 4750-4756.
D. Heckmann, et al., "Probing Integrin Selectivity: Rational Design of Highly Active and Selective Ligands for the a5b1 and avb3 Integrin Receptor." Angew. Chem. Int. Ed. 2007, 46, 3571-3574.
A.N. Bigley, et al., "Variants of Phosphotriesterase for the Enhanced Detoxification of the Chemical Warfare Agent VR." Biochemistry 2015, 54, 5502-5512.
W. Tang, et al., "Mono-acylation of symmetric diamines in the presence of water." Tetrahedron Letters 49 (2008) 6003-6006.
P.V. Ramachandran et al., "Open-Flask Synthesis of Amine-Boranes via Tandem Amine-Ammonium Salt Equilibration-Metathesis." Inorg. Chem. 2015, 54, 5618-5620.

* cited by examiner

*Primary Examiner* — Jafar Parsa
*Assistant Examiner* — Amy C Bonaparte
(74) *Attorney, Agent, or Firm* — Purdue Research Foundation; Liang Zeng Yan

(57) ABSTRACT

Disclosed herein is the preparation of functional group containing amine-boranes from the corresponding amines. The mild reaction conditions allow for the direct preparation of several hitherto inaccessible amine-boranes containing a functional moiety, such as but not limited to, alkene, alkyne, hydroxyl, thiol, acetal, ester, amide, nitrile, nitro, and alkoxysilane.

9 Claims, No Drawings

AMINE-BORANES BEARING BORANE-INTOLERANT FUNCTIONALITIES

CROSS-REFERENCE TO RELATED APPLICATIONS

The present U.S. patent application is related to and claims the priority benefit of U.S. Provisional Patent Application Ser. No. 62/377,290, filed Aug. 19, 2016, the contents of which are hereby incorporated by reference in their entirety into the present disclosure.

TECHNICAL FIELD

The present invention relates to a process for the preparation of an amine-borane, specifically, an amine-borane bearing a functionality, such as alkene, alkyne, hydroxyl, thiol, acetal, ester, amide, nitrile, nitro, or alkoxysilane, under mild conditions. Products of this facile process are also in the scope of this disclosure.

BACKGROUND

This section introduces aspects that may help facilitate a better understanding of the disclosure. Accordingly, these statements are to be read in this light and are not to be understood as admissions about what is or is not prior art.

Amine-boranes have gained considerable importance as potential candidates for hydrogen storage. Moreover, they have been evaluated as reagents in organic chemistry and materials chemistry. (Carboni and Monnier, *Tetrahedron*, 1999, 55, 1197; Staubitz, et al., *Chem. Rev.* 2010, 110, 4023) Amine-boranes have also shown promise as safe energetic materials. (Ramachandran et al., *Chem. Eur. J.* 2014, 20, 16869)

Current approaches to amine-boranes from amines include exchange with borane-Lewis base complexes or metathesis of alkylammonium salts with metal borohydrides. The former necessitates the use of moisture-sensitive and pyrophoric borane-tetrahydrofuran (BTHF) or borane-dimethyl sulfide (BMS), or harsh reaction conditions with the stable borane-ammonia complex (AB). The poor solubility of sodium borohydride and alkylammonium salts in common organic solvents severely restricts the generality of the metathesis protocol. To circumvent these, we recently discovered and disclosed a scalable protocol to access amine-boranes via an in situ generation of carbonic acid from sodium bicarbonate and water (Ramachandran et al., U.S. Patent application 2016/0101984, dated Apr. 14, 2016).

Despite these advances in their synthesis and application, borane complexes of amines bearing functional groups are rare. This also restricts the use of borane as an amine-protecting group for organic chemistry applications. Thus, a convenient approach to functionalized amine-boranes would be highly appreciated by the scientific community.

SUMMARY OF INVENTION

The present invention relates to a process for the preparation of an amine-borane complex, specifically, an amine-borane bearing a functionality, such as alkene, alkyne, hydroxyl, thiol, acetal, ester, amide, nitrile, nitro, alkoxysilane, etc., under mild conditions. Products of this facile process are also in the scope of this disclosure.

In some aspects, this invention relates to a process for the preparation of an amine-borane bearing a functionality by the steps of a. adding about two equivalent of sodium borohydride and four equivalents of sodium bicarbonate;
b. adding about one equivalent amine, wherein said amine may carry a functional group selected from the group consisting of alkene, alkyne, nitro, hydroxyl, thiol, cyano (nitrile), acetal, ester, amide, and alkoxysilane;
c. adding THF (tetrahydrofuran) with stirring to afford a reaction mixture of said amine at about 0.5~2 M (moles/liter);
d. adding about 3~4 equivalents of water in a THF solution dropwise to the reaction mixture of step c under vigorous stirring; and
e. stirring for about 4 to 48 hours to afford an amine-borane, wherein said amine-borane carries a functional group selected from the group consisting of alkene, alkyne, nitro, hydroxyl, thiol, cyano (nitrile), acetal, ester, amide, and alkoxysilane.

In some aspects, this invention relates to a process for the preparation of an amine-borane bearing a functionality by the process disclosed herein, wherein said amine-borane carries one or more functional groups selected from the group consisting of alkene, alkyne, nitro, hydroxyl, thiol, cyano (nitrile), acetal, ester, amide, and alkoxysilane.

In some other aspects, this invention relates to a functionality-bearing amine-borane synthesized by the following process:

a. adding about two equivalent of sodium borohydride and four equivalents of sodium bicarbonate;
b. adding about one equivalent amine, wherein said amine may carry a functional group selected from the group consisting of, but not limited to alkene, alkyne, nitro, hydroxyl, thiol, cyano (nitrile), acetal, ester, amide, and alkoxysilane;
c. adding THF (tetrahydrofuran) with stirring to afford a reaction mixture of said amine at about 0.5~2 M (moles/liter);
d. adding about 3~4 equivalents of water in a THF solution dropwise to the reaction mixture of step c under vigorous stirring; and
e. stirring for about 4 to 48 hours to afford an amine-borane, wherein said amine-borane carries a functional group selected from the group consisting of alkene, alkyne, nitro, hydroxyl, thiol, cyano (nitrile), acetal, ester, amide, and alkoxysilane.

In some aspects, this invention relates to an amine-borane bearing one or more functional groups selected from the group consisting of alkene, alkyne, nitro, hydroxyl, thiol, cyano (nitrile), acetal, ester, amide, and alkoxysilane.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 80%, within 90%, within 95%, or within 99% of a stated value or of a stated limit of a range.

Disclosed herein is the preparation of functional group containing amine-boranes from the corresponding amines.

The mild reaction conditions allow direct preparation of several hitherto inaccessible amine-boranes containing a functional moiety such as, but not limited to alkene, alkyne, hydroxyl, thiol, acetal, ester, amide, nitrile, nitro, and alkoxysilane.

In some illustrative embodiments, this present invention relates to a process for preparing an amine-borane, comprising the steps of
    a. adding about two equivalent of sodium borohydride and about four equivalents of sodium bicarbonate;
    b. adding about one equivalent amine, wherein said amine may carry a functional group selected from the group consisting of, but not limited to alkene, alkyne, nitro, hydroxyl, thiol, cyano (nitrile), acetal, ester, amide, and alkoxysilane;
    c. adding THF (tetrahydrofuran) with stirring to afford a reaction mixture of said amine at about 0.5~2 M (moles/liter);
    d. adding dropwise about 3~4 equivalents of water in a THF solution to the reaction mixture of step c under vigorous stirring; and
    e. stirring for about 4 to 48 hours to afford an amine-borane, wherein said amine-borane carries a functional group selected from the group consisting of, but not limited to alkene, alkyne, nitro, hydroxyl, thiol, cyano (nitrile), acetal, ester, amide, and alkoxysilane.

In some illustrative embodiments, this present invention relates to a process for preparing an amine-borane disclosed herein, wherein water-THF solution is about 14% (v/v) water in THF.

In some illustrative embodiments, this present invention relates to a process for preparing an amine-borane disclosed herein, wherein said amine is a monoamine or a diamine.

In some illustrative embodiments, this present invention relates to a process for preparing an amine-borane disclosed herein, wherein said process is performed at an ambient temperature.

In some illustrative embodiments, this present invention relates to a process for preparing an amine-borane disclosed herein, wherein said amine-borane is part of an aromatic molecule, an aliphatic molecule, or a combination thereof.

In some illustrative embodiments, this present invention relates to a process for preparing an amine-borane disclosed herein, wherein said amine-borane is part of a cyclic structure, a linear structure, a branched structure, or a combination thereof.

In some illustrative embodiments, this present invention relates to a process for preparing an amine-borane disclosed herein, wherein said water in a THF solution is about four equivalents of said amine when said amine carries a functional group selected from the group consisting of, but not limited to alkene, alkyne, nitro, hydroxyl, thiol, cyano (nitrile), acetal, ester, amide, and alkoxysilane.

In some aspects, this invention relates to a process for the preparation of an amine-borane bearing one or more functional groups selected from the group consisting of alkene, alkyne, nitro, hydroxyl, thiol, cyano (nitrile), acetal, ester, amide, and alkoxysilane.

In some illustrative embodiments, this present invention relates to an amine-borane prepared according to the process of
    a. preparing about two equivalent of sodium borohydride and about four equivalents of sodium bicarbonate;
    b. adding about one equivalent amine, wherein said amine may carry a functional group selected from the group consisting of, but not limited to alkene, alkyne, nitro, hydroxyl, thiol, cyano (nitrile), acetal, ester, amide, and alkoxysilane;
    c. adding THF (tetrahydrofuran) with stirring to afford a reaction mixture of said amine at about 0.5~2 M (moles/liter);
    d. adding dropwise about 3~4 equivalents of water in a THF solution to the reaction mixture of step c under vigorous stirring; and
    e. stirring for about 4 to 48 hours to afford an amine-borane, wherein said amine-borane may carry a functional group selected from the group consisting of, but not limited to alkene, alkyne, nitro, hydroxyl, thiol, cyano (nitrile), acetal, ester, amide, and alkoxysilane.

In some illustrative embodiments, this present invention relates to an amine-borane prepared according to the process disclosed herein, wherein said process is carried out at an ambient temperature.

In some illustrative embodiments, this present invention relates to an amine-borane prepared according to the process disclosed herein, wherein the water-THF solution is about 14% (v/v) water in THF.

In some illustrative embodiments, this present invention relates to an amine-borane prepared according to the process disclosed herein, wherein said amine may be a monoamine or a diamine.

In some illustrative embodiments, this present invention relates to an amine-borane prepared according to the process disclosed herein, wherein said amine-borane is part of an aromatic molecule, an aliphatic molecule, or a combination thereof.

In some illustrative embodiments, this present invention relates to an amine-borane prepared according to the process disclosed herein, wherein said amine-borane is part of a cyclic structure, a linear structure, a branched structure, or a combination thereof.

In some illustrative embodiments, this present invention relates to an amine-borane prepared according to the process disclosed herein, wherein said water in a THF solution is about four equivalents of said amine when said amine carries a functional group selected from the group consisting of, but not limited to alkene, alkyne, nitro, hydroxyl, thiol, cyano (nitrile), acetal, ester, amide, and alkoxysilane.

In some aspects, this invention relates to an amine-borane bearing one or more functional groups selected from the group consisting of alkene, alkyne, nitro, hydroxyl, thiol, cyano (nitrile), acetal, ester, amide, and alkoxysilane.

The following examples and specific embodiments are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

We recently realized an amine-ammonium salt equilibration-metathesis sequence to access amine-boranes under open-flask conditions (Scheme 1, Ramachandran, et al., *Inorg. Chem.* 2015, 54, 5618). Although formation of the alkylammonium sulfate intermediate occurred at ambient conditions, elevated temperatures were necessary to transaminate the byproduct AB formed via a competing pathway.

Scheme 1. Prior Methods to acess Amine-Boranes (Ramachandran, et al., *Inorg. Chem.* 2015, 54, 5618).

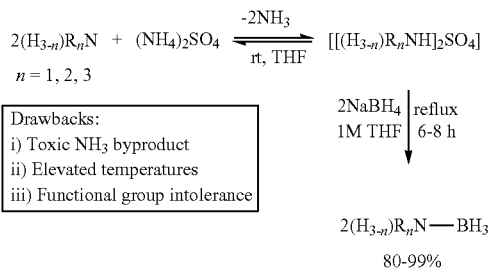

Drawbacks:
i) Toxic NH₃ byproduct
ii) Elevated temperatures
iii) Functional group intolerance Scheme 2. Methods Disclosed herein to acess Amine-Boranes

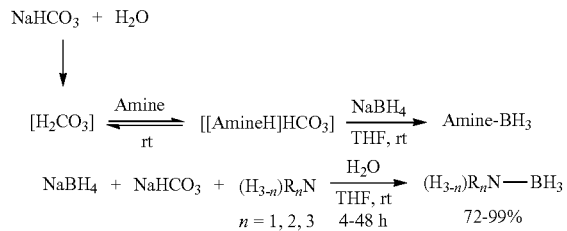

Advantages:
i) Environmentally benign reagents
ii) Ambient reaction conditions
iii) Functional group tolerance We envisaged that mild acids, such as carbonic acid, prepared from sodium bicarbonate and water (K. Adamczyk, M. Premont-Schwarz, D. Pines, E. Pines and E. T. J. Nibbering, *Science*, 2009, 326, 1690), in the presence of an amine could provide alkylammonium bicarbonate in situ. This would then undergo metathesis with $NaBH_4$ at room temperature to provide the corresponding amine-borane (Scheme 2). Key to the success of our plan would be the capture of carbonic acid by amine prior to its ready decomposition and the stability of $NaBH_4$ under mildly acidic reaction conditions. The increased probability of a facile salt metathesis due to the solubilization of $NaBH_4$ and alkylammonium bicarbonate in wet solvent looked promising. Treating an equiv. each of $NaBH_4$ and N,N,N-triethylamine (1a) with two equiv. of $NaHCO_3$ in 1 M THF-H2O (1:1 v/v) for 1 h revealed, by $^{11}B$ NMR spectroscopy, complete consumption of $NaBH_4$ and the presence of ca. 3:1 mixture of N,N,N-triethylamine-borane ($Et_3N$—$BH_3$, $^{11}B$: δ -14 ppm, 2a) and two impurities, probably hydrolysis byproducts (δ 8 and δ 18 ppm). When the quantity of water was limited to one equiv., the impurities were completely suppressed and pure 2a was isolated in 77% yield. Lowering the equiv. of $NaHCO_3$ led to longer reaction times and lower yields. The order of addition was critical. Adding amine to a mixture of $NaBH_4$, $NaHCO_3$, and water in THF resulted in the borohydride hydrolysis products. $Na_2CO_3$ was found ineffective for this transformation. Efforts to improve the yield of 2a by screening several mono and dibasic sodium and potassium salts of mineral acids proved futile. Replacing $NaBH_4$ with $KBH_4$ also led to slow reactions and poor yields. Increasing the reaction concentration to 2 or 4 M or using diethyl ether as the solvent did not afford appreciable alteration.

Finally, a reaction with 2 equiv. of $NaHCO_3$ in 2 M THF was chosen for further improvement. On the basis of our envisioned pathway (Scheme 2), water should play a critical role in promoting the reaction. Indeed, a reaction without water, even after 2 d, yielded only traces of 2a. Introducing 0.5 equiv. water completed the reaction, albeit slowly, within 24 h. Conversely, increasing the water content to 2 equiv. accelerated the reaction dramatically, complete within 1 h, to yield 82% 2a. Further increase in water content was detrimental to the yield. Less than quantitative yields of 2a remained a concern. To investigate the same, the filter cake was dissolved in water and analyzed by $^{11}B$ NMR spectroscopy, which revealed the presence of a borate salt (δ 8 ppm). This was attributed to the hydrolysis of a portion of $NaBH_4$ under the mildly acidic conditions. To ensure complete conversion to amine-borane, the effect of excess $NaBH_4$ was studied. 4-(Dimethylamino) pyridine (DMAP, 1b), a high-boiling amine, was chosen to prevent loss of residual amine during workup. At least 1.5 equiv. of $NaBH_4$ was necessary for quantitative conversion to DMAP-borane complex (2b). Significantly, even with excess $NaBH_4$, no borane complexation was observed at the less nucleophilic nitrogen in DMAP.

The putative lack of formation of free borane persuaded us to subject amines containing borane-susceptible functionalities to the new synthesis, after a minor reoptimization of the reagent equivalencies (Table 1). Alkenyl and alkynyl amines, with an exposed hydroboration site, were examined first.9 Gratifyingly, allylamine (1q), 1,2,3,6-tetrahydropyridine (1r), and propargylamine (1s) yielded the corresponding amine-boranes 2q, 2r, and 2s in 96%, 73%, and 87%, respectively, within 4 h. Delightfully, even amines containing the protic hydroxyl moiety, such as, 2-(hydroxymethyl) pyridine (1t), 3-aminopropan-1-ol (1u), and (S)-(+)-2-(hydroxymethyl)pyrrolidine (1v), underwent borane protection yielding 2t, 2u, and 2v, respectively, in good yields after chromatographic purification.11 This represents the first general route to hydroxyl-containing amine-boranes from the corresponding amino alcohols.

Extending the protocol to the more acidic thiol moiety in 2-diethylaminoethanethiol (1w) provided the borane adduct 2w in high yields with a minor amount of the disulfide linked amine-borane, which could be readily separated by column chromatography. Amines containing the aldehyde and ketone functionalities were, unfortunately, not compatible and provided the reduced borane protected aminoalcohols. Dimethylaminoacetaldehyde acetal (1x), a protected aldehyde, when subjected to the reaction conditions, yielded 96% of 2x. Pleasantly, the carbonyl moiety in the ester and amide functionalities in methyl 6-aminohexanoate (1y) and N-(3-aminopropyl)benzamide (1z) was well-tolerated, furnishing 2y and 2z in 84% and 86% yields, respectively. The nitrile group in 3-(dimethylamino)propanenitrile (1aa) also remained unaltered under the reaction conditions providing the corresponding amine-borane 2aa in 86% yield. Neither the nitrile-borane nor nitrile reduction products were observed.

Finally, we subjected 2-(4-nitrophenyl)ethylamine (1ab), an amine containing a nitro group, to our protocol, which underwent facile borane protection to yield 2ab in 86% yield. Notably, the amineboranes synthesized above represent stable molecules containing potentially incompatible electrophilic and nucleophilic centers in proximity.

The uniqueness of our robust and mild protocol was demonstrated by the facile synthesis of the vitronectin inhibitor synthon 4 (Scheme 3). The presence of the protic hydroxyl group was an impediment to its ready synthesis earlier. Our NaHCO$_3$/water-mediated protocol described herein provides a direct route to 4 in 80% yield from pyridinylamino alcohol 3 via the selective protection of the pyridine ring. The ready access to functionalized amine-boranes offered a new class of unexplored, reactive reagents for surface functionalization.

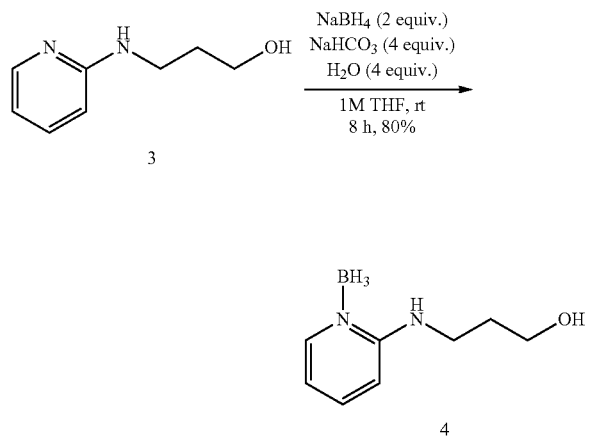

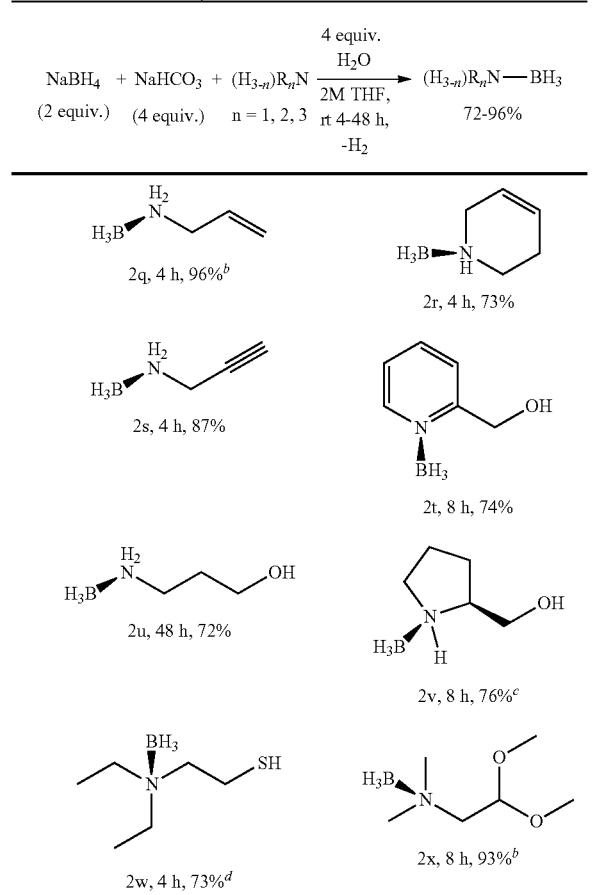

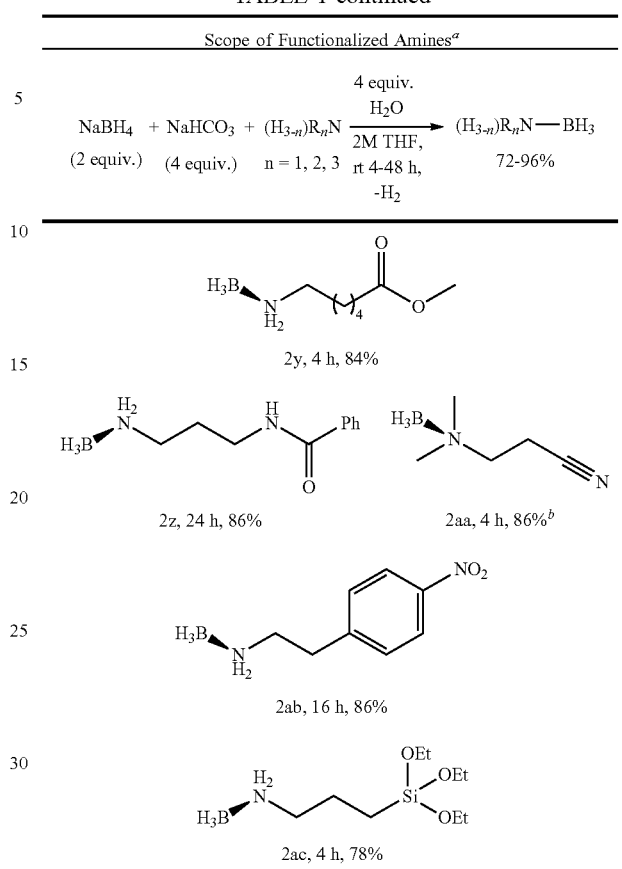

[a] Yields of isolated product.
[b] 1.5 equiv. NaBH$_4$, 3 equiv. NaHCO$_3$, and 3 equiv. water were used for 1 equiv. of amine.
[c] Diastereomeric ratio = 92:8 (by $^{11}$B NMR spectroscopy).
[d] 20% disulfide containing amine-borane was formed.

In conclusion, a general, convenient, inexpensive, and scalable protocol for the synthesis of a variety of amine-boranes in excellent yields from sodium borohydride, sodium bicarbonate, and amines in wet THF has been developed. Under these environmentally benign, mild reaction conditions, several functional groups susceptible to BTHF or BMS, such as alkene, alkyne, hydroxyl, thiol, ester, amide, nitrile, and nitro are well tolerated. Some of these functionalized amine-boranes represent stable molecules bearing potentially incompatible electrophilic and nucleophilic groups in proximity. This water-promoted synthesis has allowed access to a novel class of amine-borane based organic ligands with unique properties for surface functionalization, as demonstrated by the formation of self-assembled layers of thiol- and alkoxysilane-bearing amine-boranes on gold and silica surfaces, respectively.

General Experimental Procedures $^{11}$B, $^1$H, and $^{13}$C NMR spectra were recorded at room temperature, on a Varian INOVA 300 MHz or Bruker 400 MHz NMR spectrophotometer. Chemical shifts (δ values) are reported in parts per million relative to BF$_3$.Et$_2$O for $^{11}$B NMR respectively. Data are reported as: δ value, multiplicity (s=singlet, d=doublet, t=triplet, q=quartet, p=pentet, h=hextet, m=multiplet, br=broad) and integration. High Resolution Mass Spectra (HRMS) were recorded on a Thermo Electron Corporation MAT 95XP-Trap spectrometer. Thin-layer chromatography was carried out on 0.20 mm silica plates (G/UV$_{254}$) using UV light or Iodine as visualizing agent. Flash chromatography was performed using silica gel 40-63 um, 60 Å and dichloromethane-methanol mixture as eluent.

All solvents for routine isolation of products and chromatography were reagent-grade. Tetrahydrofuran (THF, ACS grade containing 0.004% water and 0.025% BHT) was purchased from Fisher-Scientific. Sodium borohydride (powder, purity >99% by hydride estimation1) was purchased in bulk from Dow Chemical Co. (Rohm and Haas). Sodium bicarbonate (ACS reagent, Macron), sodium carbonate (Anhydrous, Macron), sodium bisulfite (Purified, Mallinckrodt), sodium hydrogen sulfate (tech. grade, Sigma-Aldrich), potassium bicarbonate (ACS, Sigma-Aldrich), dipotassium hydrogen phosphate (Anhydrous, Fluka), and potassium dihydrogen phosphate (Assay >99.5%, Fluka) were purchased from the respective commercial sources and powdered prior to use. Amines used were purchased from commercial sources. Methyl 6-aminohexanoate (1y) (Brehm and Breinbauer, *Org. Biomol. Chem.*, 2013, 11, 4750.); N-(3-aminopropyl)benzamide (1z) (Tang and Fang, *Tetrahedron Lett.*, 2008, 49, 6003); 3-(pyridin-2-ylamino)propanol (3) (Heckmann, et al., *Angew. Chem. Int. Ed.*, 2007, 46, 3571) was prepared in accordance with literature reports. 2-Diethylaminoethanethiol (1w) (Bigley, et al., *Biochemistry*, 2015, 54, 5502); and 2-(4-nitrophenyl)ethylamine (1ab) (Maruyama, et al., U.S. Pat. No. 6,346,532 (2002)) were synthesized from their hydrochloride salts. Liquid amines were distilled while solid amines were used without any purification.

General Procedure for the Preparation of Functionalized Amine-Boranes (2a, 2p, 2r-2w, 2y-2z, 2ab-2ac, and 4):

Sodium borohydride (0.38 g, 10 mmol) and powdered sodium bicarbonate (1.68 g, 20 mmol) were transferred to a 50 mL dry round bottom flask, charged with a magnetic stir-bar. The corresponding amine (1a, 1p, 1r-1w, 1y-1z, 1ab-1ac, and 3, 5 mmol) was charged into the reaction flask followed by addition of reagent-grade tetrahydrofuran (2.5 mL for liquid amines/7.5 mL for solid amines) at rt. Under vigorous stirring, 2.5 mL of 14.4% v/v solution water in THF was added drop-wise to prevent excessive frothing. Reaction progress was monitored by $^{11}$B NMR spectroscopy (Note: A drop of anhydrous DMSO is added to the reaction aliquot before running the $^{11}$B NMR experiment). Upon completion of the reaction (4-48 h, as determined by $^{11}$B NMR), the reaction contents were filtered through sodium sulfate and celite and the solid residue washed with THF. Removal of the solvent in vacuo from the filtrate yielded the corresponding crude amine-borane. Amine-boranes 2a and 2p did not need any further purification. The rest were purified by column chromatography using dichloromethane/methanol mixture as eluent.

Characterization of Amine-Boranes:

Allylamine-borane (2q) Colorless oil. $^1$H NMR (300 MHz, CDCl$_3$) δ (ppm): 5.95 (ddt, J=16.7, 10.3, 6.3 Hz, 1H), 5.39-5.18 (m, 2H), 4.29-3.95 (m, 2H), 3.46-3.27 (m, 2H), 2.10-0.90 (br q, BH$_3$); $^{13}$C NMR (75 MHz, CDCl$_3$) δ (ppm): 132.3, 119.3, 51.0; $^{11}$B NMR (96 MHz, CDCl$_3$) δ (ppm): −19.81 (q, J=97.7 Hz). HRMS (CI) calcd for C$_3$H$_9$BN (M-H)$^+$: m/z, 70.0823, found 70.0826.

1,2,3,6-tetrahydropyridine-borane (2r) White solid. $^1$H NMR (400 MHz, DMSO-d$_6$) δ (ppm): 6.10 (s, 1H), 5.84-5.70 (m, 1H), 5.69-5.53 (m, 1H), 3.35-3.14 (m, 1H), 3.11-2.79 (m, 2H), 2.52-2.36 (m, 1H), 2.30-2.16 (m, 1H), 2.10-1.90 (m, 1H), 1.80-0.80 (br q, BH$_3$); $^{13}$C NMR (101 MHz, DMSO-d$_6$) δ (ppm): 124.9, 123.6, 50.1, 48.3, 23.3; $^{11}$B NMR (96 MHz, DMSO-d$_6$) δ (ppm): −14.48 (br q, J=95.0 Hz). HRMS (CI) calcd for C$_5$H$_{11}$BN (M-H)$^+$: m/z, 96.0979, found 96.0976.

Propargylamine-borane (2s) White solid. $^1$H NMR (300 MHz, DMSO-d$_6$) δ (ppm): δ 5.71 (s, 2H), 3.50-2.97 (m, 3H), 1.90-0.50 (br q, BH$_3$); $^{13}$C NMR (75 MHz, DMSO-d$_6$) δ (ppm): 79.6, 75.5, 36.2; $^{11}$B NMR (96 MHz, DMSO-d$_6$) δ (ppm): −18.69 (br q). HRMS (CI) calcd for C$_3$H$_7$BN (M-H)$^+$: m/z, 68.0666, found 68.0669.

2-(Hydroxymethyl)pyridine-borane (2t) White solid. $^1$H NMR (300 MHz, CDCl$_3$) δ (ppm): 8.65 (d, J=5.8 Hz, 1H), 8.02-7.91 (m, 1H), 7.85-7.75 (m, 1H), 7.44-7.32 (m, 1H), 5.03 (s, 2H), 3.17 (s, 1H), 3.00-1.75 (br q, BH$_3$); $^{13}$C NMR (75 MHz, CDCl$_3$) δ (ppm): 158.6, 148.8, 140.0, 123.5, 123.4, 62.5; $^{11}$B NMR (96 MHz, CDCl$_3$) δ (ppm): −15.23 (q, J=98 Hz). HRMS (CI) calcd for C$_6$H$_9$BNO (M-H)$^+$: m/z, 122.0772, found 122.0772.

3-Aminopropan-1-ol-borane (2u) Colorless oil. $^1$H NMR (400 MHz, DMSO-d$_6$) δ (ppm): 5.09 (s, 2H), 4.49 (t, J=5.0 Hz, 1H), 3.40 (q, J=5.9 Hz, 2H), 2.58-2.35 (m, 2H), 1.61 (p, J=6.5 Hz, 2H), 1.70-0.80 (br q, BH$_3$); $^{13}$C NMR (101 MHz, DMSO-d$_6$) δ (ppm): 59.6, 46.3, 32.1; $^{11}$B NMR (96 MHz, DMSO-d$_6$) δ (ppm): −19.59 (q, J=93.5 Hz). HRMS (CI) calcd for C$_3$H$_{11}$BNO (M-H)$^+$: m/z, 88.0928, found 88.0926.

(S)-(+)-2-(Hydroxymethyl)pyrrolidine-borane (2v) Colorless oil. Diastereomeric ratio=92:8 (as analyzed by $^{11}$B NMR spectroscopy). Major diastereomer: $^1$H NMR (300 MHz, CDCl$_3$) δ (ppm): 4.48 (s, 1H), 4.09 (dd, J=11.6, 3.1 Hz, 1H), 3.78-3.58 (m, 1H), 3.37 (dt, J=10.3, 6.5 Hz, 1H), 3.06 (dtd, J=10.6, 7.6, 3.5 Hz, 1H), 2.98-2.68 (m, 2H), 2.11-1.72 (m, 4H), 2.10-0.80 (br q, BH$_3$); $^{13}$C NMR (75 MHz, CDCl$_3$) δ (ppm): 66.9, 60.2, 55.3, 27.4, 23.8; $^{11}$B NMR (96 MHz, DMSO-d$_6$) δ (ppm): −16.43 (q, J=96.0 Hz). HRMS (CI) calcd for C$_5$H$_{13}$BNO (M-H)$^+$: m/z, 114.1085, found 114.1087.

2-Diethylaminoethanethiol-borane (2w) Colorless oil. $^1$H NMR (400 MHz, CDCl$_3$) δ (ppm): 2.98-2.69 (m, 8H), 1.19 (t, J=7.3 Hz, 6H), 1.95-0.95 (br q, BH$_3$); $^{13}$C NMR (101 MHz, CDCl$_3$) δ (ppm): 61.9, 53.0, 18.7, 8.7; $^{11}$B NMR (96 MHz, CDCl$_3$) δ (ppm): −13.45 (q, J=99.1, 93.3 Hz). HRMS (ESI) calcd for C$_6$H$_{17}$BNS (M-H)$^+$: m/z, 146.1175, found 146.1176.

2,2-Dimethoxy-N,N-dimethylethylamine-borane (2x) Colorless liquid. $^1$H NMR (300 MHz, CDCl$_3$) δ (ppm): 4.94-4.88 (m, 1H), 3.44-3.37 (m, 6H), 2.90-2.83 (m, 2H), 2.64 (m, 6H), 2.20-1.10 (br q, BH$_3$); $^{13}$C NMR (75 MHz, CDCl$_3$) δ (ppm): 101.3, 65.2, 54.5, 53.0; $^{11}$B NMR (96 MHz, CDCl$_3$) δ (ppm): −9.85 (q, J=99.0 Hz). HRMS (CI) calcd for C$_6$H$_{17}$BNO$_2$ (M-H)$^+$: m/z, 146.1347, found 146.1345.

Methyl 6-aminohexanoate-borane (2y) White solid. $^1$H NMR (300 MHz, CDCl$_3$) δ (ppm): 3.87 (s, 2H), 3.68 (s, 3H), 2.81 (p, J=7.2 Hz, 2H), 2.34 (t, J=7.3 Hz, 2H), 1.75-1.56 (m, 4H), 1.44-1.31 (m, 2H), 2.10-0.80 (br q, BH$_3$); $^{13}$C NMR (101 MHz, CDCl$_3$) δ (ppm): 174.2, 51.8, 48.6, 33.8, 28.7, 26.1, 24.4; $^{11}$B NMR (96 MHz, CDCl$_3$) δ (ppm): −15.61 (q, J=98.0 Hz). HRMS (CI) calcd for C$_7$H$_{17}$BNO$_2$ (M-H)$^+$: m/z, 158.1347, found 158.1349.

N-(3-Aminopropyl)benzamide-borane (2z) White solid. $^1$H NMR (300 MHz, DMSO-d$_6$) δ (ppm): 8.53 (t, J=5.9 Hz, 1H), 7.89-7.76 (m, 2H), 7.58-7.38 (m, 3H), 5.19 (s, 2H), 3.26 (q, J=6.5 Hz, 2H), 2.56-2.36 (m, 2H), 1.74 (p, J=7.1 Hz, 2H), 1.75-0.80 (br q, BH$_3$); $^{13}$C NMR (101 MHz, DMSO-d$_6$) δ (ppm): 166.4, 134.4, 131.1, 128.3, 127.1, 45.4, 36.7, 28.3; $^{11}$B NMR (96 MHz, DMSO-d$_6$) δ (ppm): −19.26 (br, BH$_3$). HRMS (CI) calcd for C$_{10}$H$_{16}$BN$_2$O (M-H)$^+$: m/z, 191.1350, found 191.1348.

3-(Dimethylamino)propanenitrile-borane (2aa) Colorless liquid. $^1$H NMR (300 MHz, CDCl$_3$) δ (ppm): 3.11-2.88 (m, 4H), 2.66 (s, 6H), 2.19-0.94 (br q, BH$_3$); $^{13}$C NMR (75 MHz, CDCl$_3$) δ (ppm): 117.4, 59.5, 52.5, 14.2; $^{11}$B NMR (96 MHz, CDCl$_3$) δ (ppm): −10.96 (q, J=98.6 Hz). HRMS (CI) calcd for C$_5$H$_{12}$BN$_2$ (M-H)$^+$: m/z, 111.1088, found 111.1087.

2-(4-Nitrophenyl)ethylamine-borane (2ab) White solid. $^1$H NMR (400 MHz, DMSO-d$_6$) δ (ppm): 8.10 (d, J=8.6 Hz, 2H), 7.45 (d, J=8.4 Hz, 2H), 5.32 (s, 2H), 2.93 (dd, J=9.5, 6.4 Hz, 2H), 2.76-2.58 (m, 2H), 1.85-0.80 (br q, BH$_3$); $^{13}$C NMR (101 MHz, DMSO-d$_6$) δ 147.1, 146.2, 129.9, 123.6, 48.3, 33.9; $^{11}$B NMR (96 MHz, DMSO-d$_6$) δ (ppm): −19.58 (q, J=101.7, 95.1 Hz). HRMS (ESI) calcd for C$_8$H$_{12}$BN$_2$O$_2$ (M-H)$^+$: m/z, 179.0992, found 179.0992.

(3-Aminopropyl)triethoxysilane-borane (2ac) Colorless liquid. $^1$H NMR (400 MHz, CDCl$_3$) δ (ppm): 3.99-3.88 (m, 2H), 3.84 (qd, J=7.0, 2.9 Hz, 6H), 2.82 (ddt, J=10.6, 6.9, 4.1 Hz, 2H), 1.76 (pd, J=7.1, 3.0 Hz, 2H), 1.24 (td, J=7.0, 2.9 Hz, 9H), 0.66 (td, J=7.8, 3.0 Hz, 2H), 2.10-1.10 (br q, BH$_3$); $^{13}$C NMR (101 MHz, CDCl$_3$) δ (ppm): 58.8, 50.9, 22.6, 18.4, 7.7; $^{11}$B NMR (96 MHz, CDCl$_3$) δ (ppm): −19.95 (q, J=100.5 Hz). HRMS (ESI) calcd for C$_9$H$_{26}$BNO$_3$SiNa (M+Na)$^+$: m/z, 257.1709, found 257.1711.

3-(Pyridin-2-ylamino)propan-1-ol-borane (4) Colorless oil. $^1$H NMR (300 MHz, CDCl$_3$) δ (ppm): 8.09 (d, J=6.2 Hz, 1H), 7.57 (t, J=9.0 Hz, 1H), 6.64 (d, J=8.8 Hz, 1H), 6.54 (t, J=6.6 Hz, 1H), 6.41 (s, 1H), 3.79 (t, J=5.9 Hz, 2H), 3.42 (q, J=6 Hz, 2H), 2.55 (s, 1H), 1.92 (p, J=6 Hz, 2H), 2.80-1.50 (br q, BH$_3$); $^{13}$C NMR (75 MHz, CDCl$_3$) δ (ppm): 154.6, 145.9, 139.8, 111.2, 107.2, 59.9, 39.9, 31.5; $^{11}$B NMR (96 MHz, CDCl$_3$) δ (ppm): −17.92 (q, J=97.5, 91.7 Hz). HRMS (CI) calcd for C$_8$H$_{14}$BN$_2$O (M-H)$^+$: m/z, 165.1194, found 165.1189.

General Procedure for Hydride Analysis of Amine-Boranes (Hydrolysis Reaction):

An aqueous solution of amine-borane (2 mmol in 1 mL H$_2$O) was transferred to a round bottom flask with a septum inlet fitted with a connecting tube. The connecting tube was attached to an analytical gas burette filled with CuSO$_4$ solution. A solution of RuCl$_3$ (4.2 mg, 1 mol % in 2 mL H$_2$O) was syringed into the vial, all at once. The hydrogen generated was measured using the analytical gas burette. The temperature of the reaction was maintained at 25° C.

Those skilled in the art will recognize that numerous modifications can be made to the specific implementations described above. The implementations should not be limited to the particular limitations described. Other implementations may be possible.

What is claimed is:

1. A process for preparing an amine-borane, comprising the steps of
   a. preparing about two equivalents of sodium borohydride and about four equivalents of sodium bicarbonate;
   b. adding about one equivalent of an amine, wherein said amine comprises a functional group selected from the group consisting of alkene, alkyne, nitro, hydroxyl, thiol, cyano (nitrile), acetal, ester, amide, and alkoxysilane;
   c. adding THF (tetrahydrofuran) while stirring to afford a reaction mixture of said amine in a concentration of about 0.5~2 M (moles/liter);
   d. adding about 3-4 equivalents of water in a THF solution dropwise to the reaction mixture of step c under vigorous stirring; and
   e. stirring for about 4 to 48 hours to afford an amine-borane, wherein said amine-borane comprises a functional group selected from the group consisting of alkene, alkyne, nitro, hydroxyl, thiol, cyano (nitrile), acetal, ester, amide, and alkoxysilane.

2. The process of claim 1, wherein the water-THF solution is about 14% (v/v) water in THF.

3. The process of claim 1, wherein said amine is a monoamine or a diamine.

4. The process of claim 1, wherein said process is performed at an ambient temperature.

5. The process of claim 1, wherein said amine-borane is part of an aromatic molecule, an aliphatic molecule, or a combination thereof.

6. The process of claim 1, wherein said amine-borane is part of a cyclic structure, a linear structure, a branched structure, or a combination thereof.

7. The process of claim 1, wherein said water in a THF solution is about four equivalents of said amine when said amine comprises a functional group selected from the group consisting of alkene, alkyne, nitro, hydroxyl, thiol, cyano (nitrile), acetal, ester, amide, and alkoxysilane.

8. The process of claim 1, wherein said amine comprises two or more functional groups selected from the group consisting of alkene, alkyne, nitro, hydroxyl, thiol, cyano (nitrile), acetal, ester, amide, and alkoxysilane.

9. The process of claim 1, wherein said amine-borane comprises two or more functional groups selected from the group consisting of alkene, alkyne, nitro, hydroxyl, thiol, cyano (nitrile), acetal, ester, amide, and alkoxysilane.

* * * * *